(12) United States Patent
Alexandre et al.

(10) Patent No.: US 6,835,187 B2
(45) Date of Patent: Dec. 28, 2004

(54) NEEDLELESS SYRINGE PROVIDED WITH AN INNER SEAL CONTAINING THE ACTIVE PRINCIPLE

(75) Inventors: Patrick Alexandre, Gray (FR); Georges Baud, La Crau (FR); Philippe Gautier, Le Plessis Pate (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 0 days.

(21) Appl. No.: 10/169,792

(22) PCT Filed: Jan. 26, 2001

(86) PCT No.: PCT/FR01/00251
§ 371 (c)(1),
(2), (4) Date: Sep. 4, 2002

(87) PCT Pub. No.: WO01/56637
PCT Pub. Date: Aug. 9, 2001

(65) Prior Publication Data
US 2003/0078536 A1 Apr. 24, 2003

(30) Foreign Application Priority Data
Feb. 2, 2000 (FR) .............................................. 00 01311

(51) Int. Cl.[7] .......................... A61M 37/00; A61M 5/30; A61M 31/00
(52) U.S. Cl. ............................. 604/82; 604/69; 604/60; 604/68; 604/141; 604/84; 604/59
(58) Field of Search ............................. 604/58–92, 116, 604/522, 143, 140–141, 131, 139, 413–148, 240, 57

(56) References Cited

U.S. PATENT DOCUMENTS

| 4,124,024 A | 11/1978 | Schwebel et al. |
| 5,478,744 A | 12/1995 | Sanford et al. |
| 5,899,880 A | 5/1999 | Bellhouse et al. |
| 6,592,545 B1 * | 7/2003 | Bellhouse et al. ............ 604/69 |
| 2002/0004641 A1 * | 1/2002 | Bellhoue |
| 2002/0188248 A1 * | 12/2002 | Bellhouse |

FOREIGN PATENT DOCUMENTS

| WO | WO 94/24263 | 10/1994 |
| WO | WO 96/12513 | 5/1996 |

* cited by examiner

*Primary Examiner*—Nicholas D. Lucchesi
*Assistant Examiner*—Roz Maiorino
(74) *Attorney, Agent, or Firm*—Oliff & Berridge, PLC

(57) ABSTRACT

The technical field of the invention is that of needleless syringes used for injecting active principles in powder form for therapeutic purposes. The invention concerns a needleless syringe (1) comprising successively a gas generator (2), a gas expanding chamber (3), means for retaining active particles and an ejection tube (4). The invention is characterised in that the particle retaining means consists of an inner seal (14) having at least a cavity (15), the inner seal (14) serves both to contain the active principle and to generate a shock wave when it is ruptured.

10 Claims, 3 Drawing Sheets

NEEDLELESS SYRINGE PROVIDED WITH AN INNER SEAL CONTAINING THE ACTIVE PRINCIPLE

The technical field of the invention is that of needleless syringes used for subdermal or intramuscular injection of various active principles in pulverulent form for therapeutic use in human or veterinary medicine.

More specifically, the invention relates to a needleless syringe using a gas generator which is intended to create a pressure wave for ejecting the particles of active principle. A burstable inner seal, placed on the pathway of the gases, makes it possible to obtain the threshold pressure level permitting ejection of the particles at a sufficiently high speed. This is because the sudden release of the gases creates a shock wave in the syringe and it is this shock which will carry and accelerate the particles in order to expel them. The specificity of the invention lies in the fact that the inner seal has another function than that of contributing to creating a shock wave: it also serves as a system for retention of the solid particles of active principle.

Needleless syringes which function by generating a shock for entraining the solid particles of active principle already exist and have been the subject of several patents. Mention may be made, in particular, of patent WO 94/24263 which describes a needleless syringe functioning by release of a reserve of gas in order to entrain the solid particles of active principle. In said patent, one of the main characteristics is that the particles are maintained permanently on the pathway of the gases, between two burstable membranes.

Other patents concerning devices other than needleless syringes describe mechanisms for ejection of solid particles. Mention may be made, for example, of patent U.S. Pat. No. 5,478,744 which concerns a device with which it is possible to bombard cell cultures with inert or biologically active particles, and whose operating principle is based on the release of a compressed gas in a tube which can be supplied with particles from the side. This same patent describes a mechanism for ejection of solid particles involving a weight which carries said particles, is accelerated under the action of the compressed gases, and is then suddenly stopped by a limit stop, allowing the particles to continue their course at high speed.

Neither of the two patents mentioned above relates to mechanisms for ejection of solid particles involving an inner seal with the double function of carrying the particles and of creating a shock wave.

The needleless syringe according to the invention is able to eject solid particles of active principle under the effect of a shock wave produced by the release of a compressed gas.

Using a pyrotechnic charge makes it possible to satisfy the double requirement of performance and reliability. This is because a powder charge can produce a large quantity of gas in a very short time and thus contribute to generating a shock wave, the speed of whose front can be very high. Consequently, the particles of active principle undergo substantial acceleration, promoting their penetrating ability, while the blast at the syringe exit dissipates very rapidly into the ambient air. In addition, the firing of miniaturized pyrotechnic charges is perfectly controlled by means of initiators which have been widely tried and tested and adapted to the characteristics of said charges to be initiated, thereby making the needleless syringes according to the invention very reliable. Finally, by using an inner seal which has the double function of containing the particles of active principle and of creating a shock wave, it is possible to reduce the size of the syringe and to simplify the operating mechanism by reducing the number of parts involved.

The subject of the present invention is a needleless syringe comprising, in succession, a gas generator, a gas expansion chamber, a means for retention of the particles of active principle, and a tube for ejection of said particles, characterized in that the means for retention of the particles is formed by an inner seal which has at least one cavity intended to house the particles, said inner seal being designed to burst at the level of this cavity when it is subjected to a threshold pressure level. The inner seal preferably has, at the level of this cavity, at least one line of weakening which is designed to promote its opening upon release of the particles. According to a preferred embodiment of the invention, the inner seal is formed by at least two symmetrical elements attached along a line of opening which permits release of the particles. One of the objects intended to be achieved by this type of configuration is a clean breaking of the inner seal in order to properly release the solid particles of active principle without production of parasite particles which may originate from the inner seal and be expelled. Moreover, since the particles of active principle are to be released just before the creation of the shock wave in the tube, or at the latest at the same time, it is therefore desirable to promote rupturing of the inner seal at the level of the cavity containing the particles of active principle. The inner seal advantageously has a transverse position in relation to the axis of the ejection tube and has, on its downstream face, a central extension in which the cavity is situated.

According to a first preferred embodiment of the invention, the inner seal is fixed and comprises a closed cavity at its center. For this configuration, the inner seal marks the boundary between the expansion chamber and the ejection tube. In this way, when the pressure in the expansion chamber reaches a threshold value, the inner seal opens at the level of its cavity, permitting release of the particles of active principle into the ejection tube and almost simultaneously provoking the creation of a shock wave in said tube.

According to a second preferred embodiment of the invention, the inner seal constitutes one of the two ends of a hollow cylinder situated in the expansion chamber. More precisely, the outer lateral wall of the hollow cylinder is in contact with the inner lateral wall of the chamber, and the inner seal is situated at that end of the cylinder farthest from the gas generator. The cavity of the inner seal is advantageously blind and is obturated by a transverse membrane fixed in the ejection tube. The transverse membrane is preferably fixed at the level of an internal shoulder marking the limit between the chamber and the ejection tube, and the hollow cylinder is held in the chamber by virtue of the membrane with which it is in contact. The inner seal is advantageously bonded to the transverse membrane. The gases emitted by the gas generator preferably cause the displacement of the hollow cylinder as far as the internal shoulder against which it abuts, this displacement entailing the rupturing of the membrane by the central extension of the innner seal as it passes through, and also immediately causing the release of the solid particles of active principle. The membrane advantageously has a small thickness and is formed by a nonelastic material. The membrane has a double function: it obturates the cavity in order to maintain the particles in their seat and also serves as a fixation surface for the hollow cylinder. The edge of the blind cavity is preferably tapered to facilitate the opening of the membrane, said membrane being pre-cut radially as far as the center in order to promote opening in the manner of petals. This membrane must be dimensioned in such a way that it does not impede the displacement of the hollow cylinder by offering too much resistance, and in such a way that it does not divide into several pieces at the moment it ruptures. According to this second preferred embodiment of the invention, the gases emitted initially provoke the displacement of the hollow cylinder, which tears the membrane and permits the release of the particles of active principle into the ejection tube. The cylinder is subsequently blocked against the internal shoulder and, when the pressure of the gases reaches a threshold value in the space between the gas generator and the inner seal, said inner seal opens, creating a shock wave.

The inner seal is advantageously calibrated to yield at a pressure of at least 20 bar, but this pressure of rupture must be adapted depending on the granulometry and the density of the particles of active principle, in such a way that the speed of ejection of the particles at the outlet of the ejection tube is greater than 750 meters per second.

According to another embodiment of the invention, the inner seal has several cavities aligned in the same direction. The inner seal preferably has a rectilinear line of weakening passing through all the cavities. By this means, all the cavities open concomitantly, permitting creation of a single intense shock wave.

The gas generator is advantageously a pyrotechnic gas generator comprising a pyrotechnic charge and a device for initiation of said charge.

The initiation device preferably comprises a percussion system and a primer currently used in the pyrotechnics industry. However, it is also possible to initiate the pyrotechnic charge by other means, and in particular those involving either a piezoelectric crystal or a roughened area or even a battery. The trigger is advantageously situated at one of the ends of the syringe in the form of a push button in order to make it easier to grip and operate.

The needleless syringes according to the invention benefit from the advantages associated with functioning by means of a shock wave, in particular in terms of the speed of ejection of the particles, while at the same time ensuring reliable maintenance of the particles in storage mode.

Moreover, the use of an inner seal having the double function of housing the particles of active principle and of creating a shock wave makes it possible to simplify the operating mechanism of the syringe by limiting the number of parts involved.

Finally, maintaining the particles in the pathway of the gases is a guarantee that all the particles of active principle will be in a position to be accelerated by the shock wave.

Two preferred embodiments of the invention are described in detail below with reference to FIGS. 1 to 47.

The terms "downstream" and "upstream" in the following detailed description are used in relation to the direction of propagation of the gases in the syringe.

Figure 1:
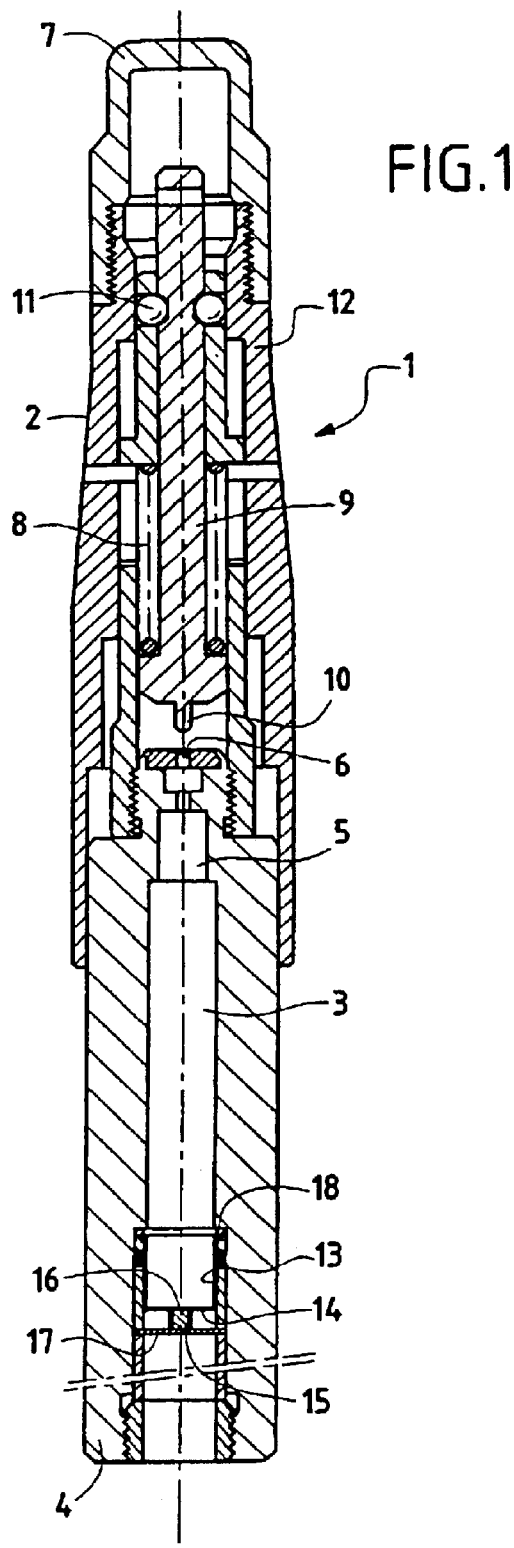
FIG. 1 is a view, in longitudinal cross section, of a needleless syringe according to the invention, having an inner seal which comprises a cavity obturated by a transverse membrane, said syringe having not yet been used.
Figure 2:
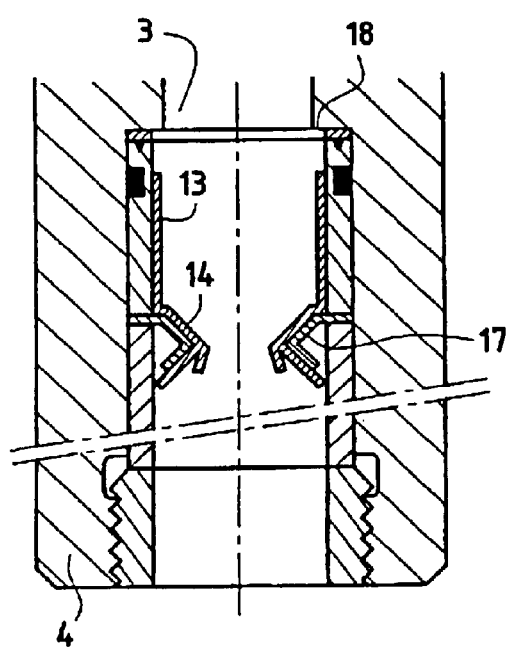
FIG. 2 is an enlarged view, in longitudinal cross section, of the system for retention of the particles of the syringe in FIG. 1, after it has been used.
Figure 3:
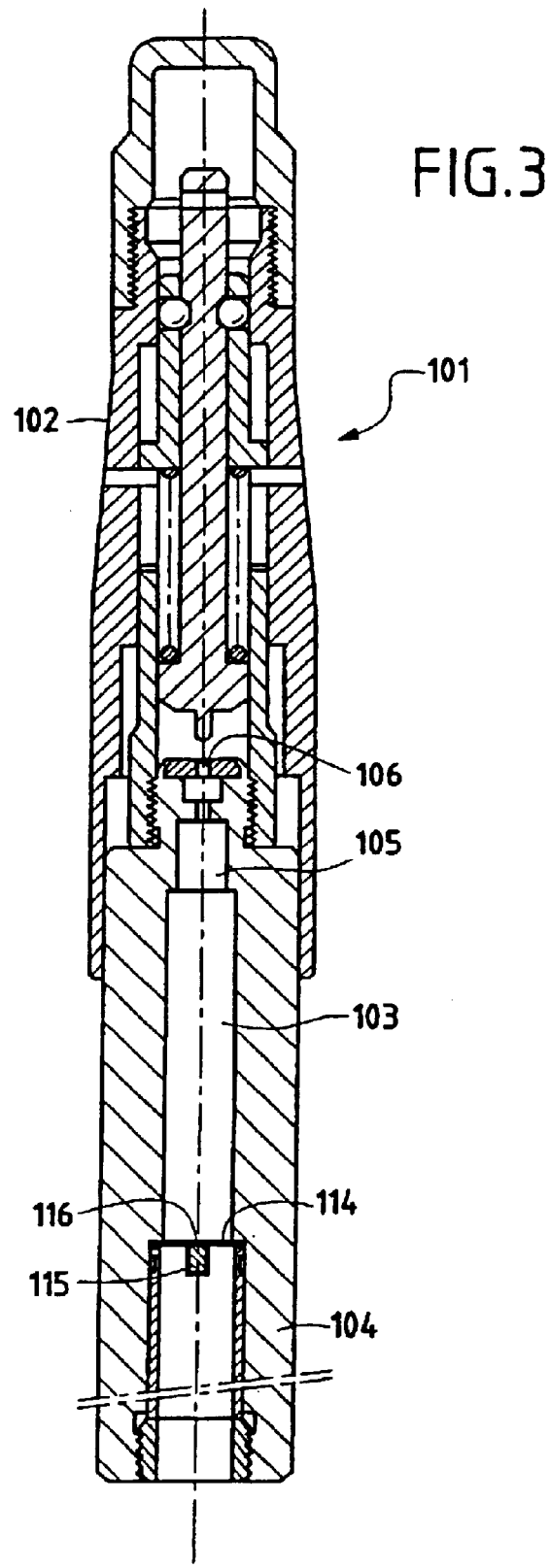
FIG. 3 is a view, in longitudinal cross section, of a needleless syringe according to the invention, having an inner seal with a closed cavity, said syringe having not yet been used.
Figure 4:
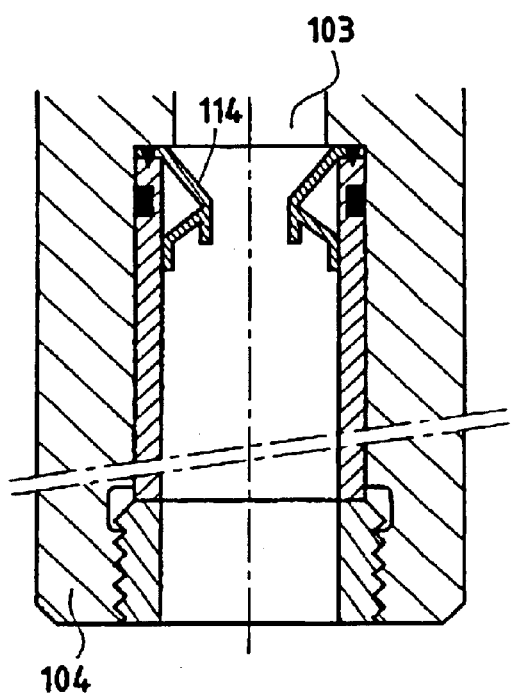
FIG. 4 is an enlarged view, in longitudinal cross section, of the system for retention of the particles of the syringe in FIG. 3 after use.

Referring to FIG. 1, a needleless syringe 1 according to the first preferred embodiment of the invention comprises, in succession, a pyrotechnic gas generator 2, an expansion chamber 3, a system for retention of the particles, and a tube 4 used for ejection of said particles and intended to bear against the skin of the patient who is to be treated.

The pyrotechnic gas generator 2 comprises an initiation device for a pyrotechnic charge 5 involving a percussion device and a primer 6. The percussion device, which is triggered by a push button 7, comprises a spring 8 and an elongate weight 9 equipped with a striker 10. The weight 9 is blocked by at least one immobilizing ball 11 wedged between said weight 9 and a hollow cylindrical body 12 in which said weight 9 can be displaced. The primer 6 and the pyrotechnic charge 5, of substantially cylindrical shape, are accommodated in the hollow cylindrical body 12 downstream of the weight 9. The pyrotechnic charge 5, which is accommodated in the hollow body 12, opens onto a free space of the syringe constituting the expansion chamber 3 for the gases which will issue from the combustion of the pyrotechnic charge 5.

The chamber 3 is delimited, at its end remote from that formed by the pyrotechnic charge 5, by a hollow cylindrical part 13, one of whose ends is free and the other of which is closed by an inner seal 14 which can burst beyond a threshold pressure level in said chamber 3.

More specifically, it is the inner seal 14 which delimits the length of the chamber 3.

The hollow cylindrical part 13 is positioned in the syringe in such a way that its end closed by the inner seal 14 is downstream of its free end. The inner seal 14 is in the form of a plane circular part having a downstream face at the center of which there is a hollow protuberance, of cylindrical shape, constituting a cavity 15 for accommodating the solid particles of active principle. The plane circular part has, at its center, in the area of the zone where the protuberance is situated, a line of weakening 16 which is directed along a diameter of said protuberance. The hollow cylindrical part 13 comprising the inner seal 14 is advantageously made of polycarbonate. An inextensible membrane 17 of small thickness, and positioned transversely with respect to the axis of the ejection tube 4, is fixed to said tube 4. This membrane can be made of polyethylene, for example.

The part 13 is placed in the syringe 1 in such a way that, on the one hand, its free end comes to bear against an internal shoulder 18 situated in the chamber 3 and, on the other hand, the central protuberance of the inner seal 14 is in contact with the transverse membrane 17. This contact can be ensured by light bonding. In this way, the cavity 15 containing the solid particles of active principle is closed by the membrane 17. The ejection tube 4 can advantageously end in a shock-absorbing rim in order to facilitate the contact of the syringe 1 on the patient's skin.

This first preferred embodiment of the invention functions in the following way.

The user positions the syringe 1 in such a way that the end of the ejection tube 4 bears against the skin of the patient who is to be treated.

Pressure on the push button 7 means, on the one hand, that the hollow cylindrical body 12 is displaced until its widened part is in line with the immobilizing ball 11, and, on the other hand, that the spring 8 is compressed. The ball 11 leaves its seat, thereby freeing the weight 9 which, subjected to the action of the spring 8 which releases, is abruptly accelerated toward the primer 6, with the striker 10 leading. The reaction of the primer 6 results in the firing of the pyrotechnic charge 5 which breaks up and emits gases, said gases instantaneously invading the expansion chamber 3 and the inside of the hollow cylindrical part 13.

Figure 5:
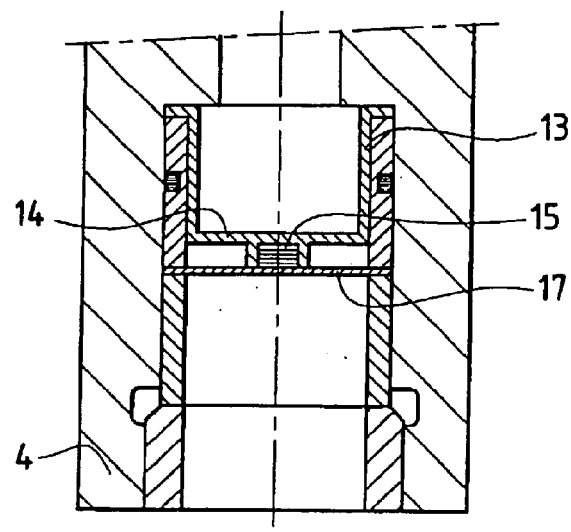
FIG. 5 is an enlarged view, in longitudinal cross section, of the system for retention of the particles of the syringe in FIG. 1 before use.
Figure 6:
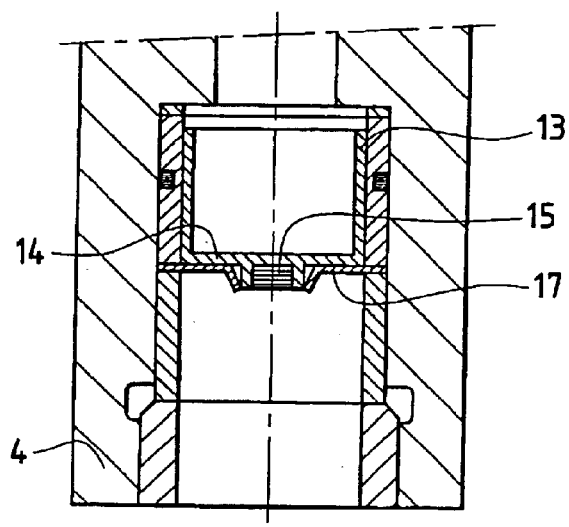
FIG. 6 is an enlarged view, in longitudinal cross section, of the system for retention of the particles of the syringe in FIG. 1, just after the pyrotechnic charge has been ignited.
Figure 7:
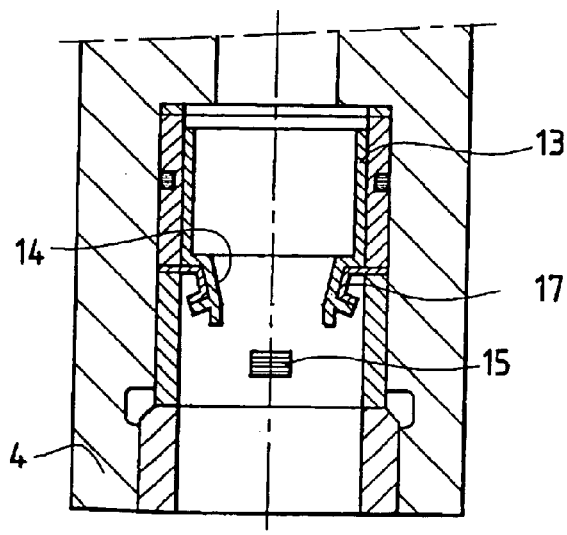
FIG. 7 is an enlarged view, in longitudinal cross section, of the system for retention of the particles of the syringe in FIG. 1 after it has been used.

As shown in FIGS. 5–7, the pressure thus generated in said chamber 3 provokes the displacement of said hollow cylindrical part 13 which tears the membrane 17 with the edge of the cavity 15, permitting the release of the solid particles of active principle in the ejection tube 4. As FIG. 6 shows, the hollow cylindrical part 13 finishes its travel when the plane circular part of the inner seal 14 comes into abutment against the peripheral edge of the membrane 17 not affected by the passage of the protuberance and extending into the tube 4. When the hollow cylindrical part 13 is thus blocked at the end of its travel, the pressure level rises in the chamber 3, and in the cylindrical part 13, until, as shown in FIG. 7, it brings about opening of the inner seal 14 along its line of weakening 16. This opening creates a shock wave in the tube 4, which shock wave entrains and accelerates the particles still in the form of a diffuse cloud. The release of the particles into the tube 4 and the opening of the inner seal 14 must take place in a very short interval, not exceeding a few milliseconds, in order to ensure that the particles have not had time to regroup as a result of inertia.

According to a second preferred embodiment of the invention, the needleless syringe comprises, in succession, a pyrotechnic gas generator 102, an expansion chamber 103, a system for retention of the particles, and a tube 104 for ejection of said particles which is intended to bear against the skin of the patient who is to be treated. The pyrotechnic gas generator 102, which functions with a percussion device, a pyrotechnic charge 105 and a primer 106, is identical in all respects to that described above for the first preferred embodiment of the invention.

Referring to FIG. 3, the expansion chamber 103 has a substantially cylindrical shape and its diameter is smaller than that of the ejection tube 104, which is also cylindrical and forms its continuation. An internal shoulder marks this difference in diameter. The chamber 103 is delimited, along its axis, on the one hand by a face in which the pyrotechnic charge 105 opens out, and on the other hand by an inner seal 114 which is liable to burst above a threshold pressure level in said chamber 103. The inner seal 114 is in the form of a plane circular part having a downstream face at the center of which there is a hollow protuberance of cylindrical shape constituting a cavity 115 for accommodating the solid particles of active principle. Said circular part has at its center, in the zone where the protuberance is situated, a line of weakening 116 directed along a diameter of said protuberance. This cavity 115 is obturated by a thin membrane so as to retain the particles. The inner seal 114 is in a transverse position with respect to the axis of the chamber 103 and of the tube 104. This inner seal, which is gripped between the internal shoulder, marking the boundary between the chamber 103 and the tube 104, and a part coming into abutment against said shoulder is nonmovable. The ejection tube 104 can advantageously end in a shock-absorbing rim facilitating the contact of the syringe on the patient's skin.

This second preferred embodiment of the invention functions as follows. The step leading to the firing of the pyrotechnic charge 105 by the user is strictly identical to that described above for the first preferred embodiment of the invention. The gases emitted by the combustion of the pyrotechnic charge 105 invade the chamber 103. The pressure in said chamber 103 rises and ends by opening the inner seal 114 along its line of weakening 116, resulting simultaneously in the release of the particles of active principle into the tube 104 and the creation of a shock wave which carries and accelerates said particles, still in the form of a diffuse cloud, toward the skin of the patient who is to be treated. The inner seal 114, once opened, is pressed flat against the inner lateral wall of the ejection tube 104.

What is claimed is:

1. A needleless syringe comprising, in succession, a gas generator, a gas expansion chamber, an inner seal with at least one cavity intended to accommodate particles, said inner seal being designed to burst in the area of this cavity when it is subjected to a threshold pressure level, and a tube for the ejection of said particles, characterized in that the inner seal constitutes one of the two ends of a hollow cylinder, the hollow cylinder being situated in the expansion chamber and capable of being displaced under the action of the gases produced by the generator, the cavity of said inner seal being blind and obturated by a transverse membrane fixed in the ejection tube.

2. The needleless syringe as claimed in claim 1, characterized in that the inner seal has, in the area of its cavity, a line of weakening which is designed to promote its opening upon release of the particles.

3. The needleless syringe as claimed in claim 1, characterized in that the inner seal is formed by at least two symmetrical elements attached along a line of opening permitting release of the particles.

4. The needleless syringe as claimed in claim 1, characterized in that the inner seal has a transverse position in relation to the axis of the ejection tube and has, on its downstream face, which is external to the cylinder, a central extension in which the cavity is situated.

5. The needleless syringe as claimed in clam 1, characterized in that the transverse membrane is fixed at the level of an internal shoulder marking the limit between the level of an internal shoulder marking the limit between the chamber and the ejection tube, and the hollow cylinder, which is held in the chamber by virtue of the membrane with which it is in contact, can come into abutment against said shoulder under the action of the gases released by the generator.

6. The needleless syringe as claimed in claim 1, characterized in that the edge of the blind cavity is tapered to facilitate the opening of the membrane, said membrane being pre-cut radially as far as the center in order to promote opening in the manner of petals.

7. The needleless syringe as claimed in claim 1, characterized in that the inner seal is calibrated to yield at a pressure of at least 20 bar.

8. The needleless syringe as claimed in claim 1, characterized in that the gas generator is a pyrotechnic gas generator comprising a pyrotechnic charge and an initiation device.

9. The needleless syringe as claimed in claim 8, characterized in that the initiation device comprises a percussion system and a primer.

10. The needleless syringe as claimed in claim 6, characterized in that the edge of the bind cavity is tapered to facilitate the opening of the membrane, said membrane being pre-cut radially as far as the center in order to promote opening in the manner of petals.

* * * * *